US009880120B2

(12) United States Patent
Ghionea et al.

(10) Patent No.: US 9,880,120 B2
(45) Date of Patent: Jan. 30, 2018

(54) ELECTRIC FIELD SENSOR

(71) Applicant: U.S. Army Research Laboratory ATTN: RDRL-LOC-I, Washington, DC (US)

(72) Inventors: Simon J. Ghionea, Laurel, MD (US); David M. Hull, Adelphi, MD (US); Gabriel L. Smith, Ellicott City, MD (US); Jeffrey S. Pulskamp, Bethesda, MD (US); Sarah S. Bedair, Bethesda, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 555 days.

(21) Appl. No.: 14/337,671

(22) Filed: Jul. 22, 2014

(65) Prior Publication Data

US 2016/0025666 A1   Jan. 28, 2016

(51) Int. Cl.
*G01N 27/26* (2006.01)
*G01R 29/12* (2006.01)

(52) U.S. Cl.
CPC ............ *G01N 27/26* (2013.01); *G01R 29/12* (2013.01)

(58) Field of Classification Search
CPC ... G01R 29/12; G01R 5/28; G01R 9/00–9/08; H01F 21/10; H01F 27/36
See application file for complete search history.

(56) References Cited

U.S. PATENT DOCUMENTS

| 8,724,200 B1* | 5/2014 | Wu | G02B 26/0825 359/224.1 |
| 2006/0261818 A1* | 11/2006 | Zank | G01V 3/088 324/457 |
| 2006/0279271 A1* | 12/2006 | Xia | G01R 29/12 324/71.1 |
| 2008/0129302 A1* | 6/2008 | Shafai | G01R 29/12 324/458 |
| 2010/0045141 A1* | 2/2010 | Pulskamp | H01L 41/0933 310/328 |

OTHER PUBLICATIONS

M. N. Horenstein and P. R. Stone, "A micro-aperture electrostatic field mill based on MEMS technology," Journal of Electrostatics, 51-52 (2001) 515-521.

(Continued)

*Primary Examiner* — Jeffrey T Barton
*Assistant Examiner* — Daniel P Malley, Jr.
(74) *Attorney, Agent, or Firm* — Eric Brett Compton

(57) ABSTRACT

According to embodiments, an electric field sensor having a sensor electrode is constructed of an electrically conductive material and having one or more outwardly protruding pillars. A screen electrode overlies the sensor electrode and has one or more openings which register with the one or more pillars on the sensor electrode. At least one piezoelectric actuator is connected to the screen electrode so that, when excited by a voltage signal, the piezoelectric actuator modulates the screen electrode toward and away from the sensor electrode at the frequency of the periodic voltage signal. An output circuit configured to detect a voltage, a current output, or both, between the sensor electrode and the screen electrode which is proportional in magnitude to the strength of the electric field.

20 Claims, 2 Drawing Sheets

(56) References Cited

OTHER PUBLICATIONS

P. S. Riehl, K. L. Scott, R. S. Muller, R. T. Howe, and J. A. Yasaitis, "Electrostatic charge and field sensors based on micromechanical resonators," Microelectromechanical Systems, Journal of, vol. 12, No. 5, pp. 577-589, 2003.
C. Gong, S. Xia, K. Deng, Q. Bai, and S. Chen, "Electric field sensors based on MEMS technology," J. of Electron. (China), vol. 22, No. 4, pp. 443-448, Jul. 2005.
A. Roncin, C. Shafai, and D. R. Swatek, "Electric field sensor using electrostatic force deflection of a micro-spring supported membrane," Sensors and Actuators A: Physical, vol. 123-124, pp. 179-184, Sep. 2005.
C. Gong, H. Tao, C. Peng, Q. Bai, S. Chen, and S. Xia, "A novel miniature interlacing vibrating electric field sensor," in 2005 IEEE Sensors, 2005.
X. Chen, C. Peng, H. Tao, C. Ye, Q. Bai, S. Chen, and S. Xia, "Thermally driven micro-electrostatic fieldmeter," Sensors and Actuators A: Physical, vol. 132, No. 2, pp. 677-682, Nov. 2006.
T. Denison, Jinbo Kuang, J. Shafran, M. Judy, and K. Lundberg, "A Self-Resonant MEMS-based Electrostatic Field Sensor with 4V/m/ Hz Sensitivity," in Solid-State Circuits Conference, 2006. ISSCC 2006. Digest of Technical Papers. IEEE International, 2006, pp. 1121-1130.
C. R. Peng, X. X. Chen, C. Ye, Q. Bai, and S. H. Xia, "Design of a Resonant Miniature Electrostatic Field Sensor with Feedback Driving and Detection," in 1st IEEE International Conference on Nano/Micro Engineered and Molecular Systems, 2006. NEMS '06, 2006, pp. 1029-1032.
C. Peng, X. Chen, Q. Bai, L. Luo, and S. Xia, "A Novel High Performance Micromechanical Resonant Electrostatic Field Sensor Used in Atmospheric Electric Field Detection," in Micro Electro Mechanical Systems, 2006. MEMS 2006 Istanbul. 19th IEEE International Conference on, 2006, pp. 698-701.
B. Bahreyni, G. Wijeweera, C. Shafai, and A. Rajapakse, "Design and Testing of a Field-Chopping Electric Field Sensor using Thermal Actuators with Mechanically Amplified Response," in Solid-State Sensors, Actuators and Microsystems Conference, 2007. Transducers 2007. International, 2007, pp. 1397-1400.
G. Wijeweera, C. Shafai, and A. Rajapakse, "Measuring power system voltage remotely using micromachined electric field sensor," in Microsystems and Nanoelectronics Research Conference, 2008. MNRC 2008. 1st, 2008, pp. 209-212.
C. Peng and S. Xia, "A novel micro-electrostatic field sensor based on parallel-plate resonator," in 4th IEEE International Conference on Nano/Micro Engineered and Molecular Systems, 2009. NEMS 2009,2009, pp. 1092-1095.
G. Wijeweera, B. Bahreyni, C. Shafai, A. Rajapakse, and D. R. Swatek, "Micromachined Electric-Field Sensor to Measure AC and DC Fields in Power Systems," Power Delivery, IEEE Transactions on, vol. 24, No. 3, pp. 988-995, 2009.
C. Peng, P. Yang, H. Zhang, X. Guo, and S. Xia, "Design of a novel closed-loop SOI MEMS resonant electrostatic field sensor," Procedia Engineering, vol. 5, pp. 1482-1485, 2010.
C. Peng, P. Yang, S. Liu, H. Zhang, K. Feng, and S. Xia, "Detecting internal defect of non-ceramic insulators using a novel micromachined electric field sensor," in Micro Electra Mechanical Systems (MEMS), 2011 IEEE 24th International Conference on, 2011, pp. 561-564.
S. G. Gathman and R. V. Anderson, "Improved Field Meter for Electrostatic Measurements," Review of Scientific Instruments 36, 1490 (1965).
S.Vinci, J. Zhu and D. Hull, "Analysis of Electrostatic Charge on Small-Arms Projectiles," Proc. of SPIE vol. 8382, 83820M, 2012.
S. Ghionea, et al., "MEMS Electric-Field Sensor With Lead Zirconate Titanate (PZT)-Actuated Electrodes," Sensors, 2013 IEEE, Nov. 3-6, 2013.

\* cited by examiner

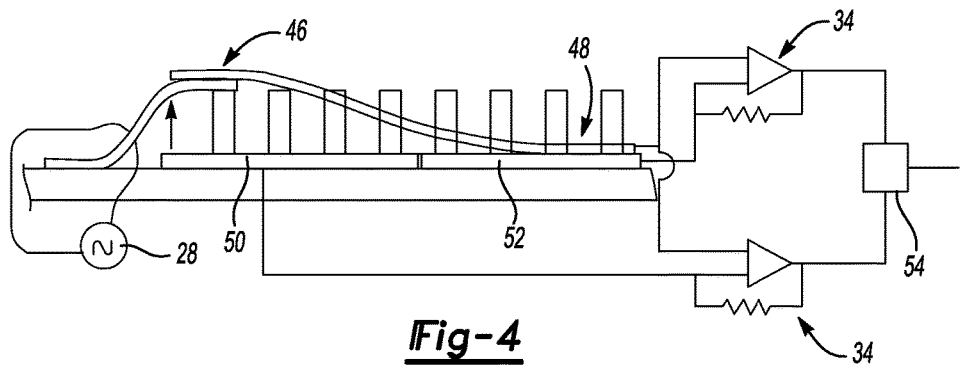
Fig-4
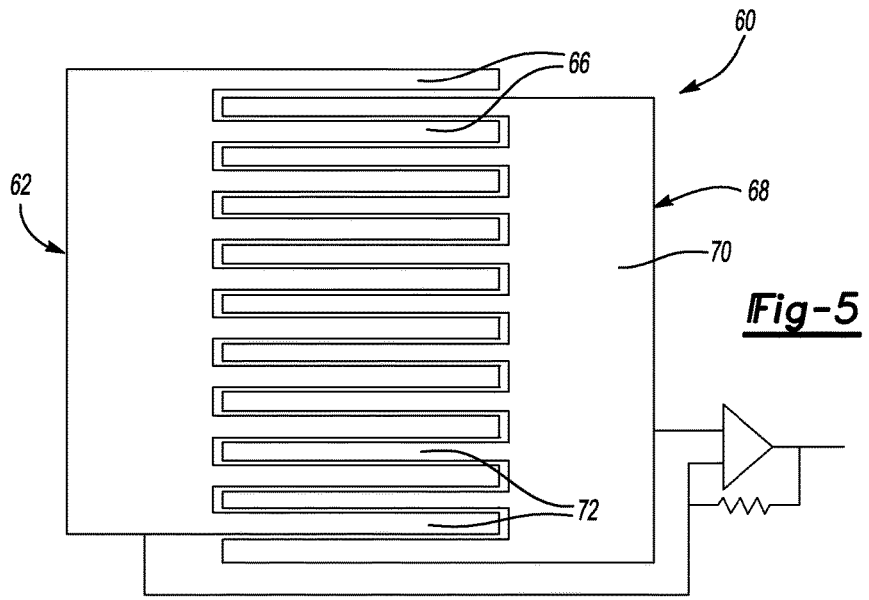
Fig-5
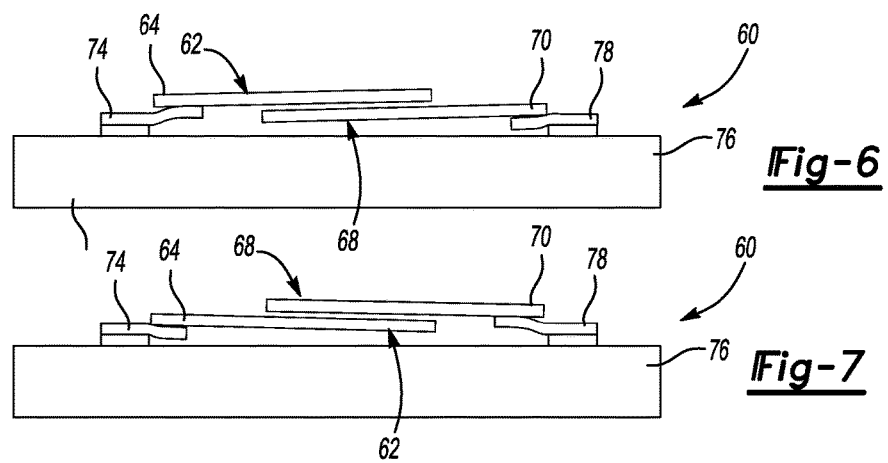
Fig-6
Fig-7

ELECTRIC FIELD SENSOR

GOVERNMENT INTEREST

The invention described herein may be manufactured, used, and licensed by or for the United States Government.

BACKGROUND OF THE INVENTION

I. Field of the Invention

The present invention relates generally to electric field sensors and, more particularly, to an electric field sensor with piezoelectric actuated electrodes.

II. Description of Related Art

Low frequency electric field sensors have found numerous industrial, medical, scientific, and military uses. The field sources typically measured in these applications are electrostatically charged particles or surfaces, atmospheric electricity, or active voltage/charge sources such as brainwaves, printed circuit components, and power lines. While there are a variety of means of measuring an ambient electric field, those electric field sensors based on galvanic measurement principles offer the advantage of relative simplicity due primarily to the use of standard metallic conductor electrodes. In the discussion that follows, "galvanic measurement" means that a voltage or current is induced on the electrodes directly by the electric field, and is measured with a sensitive preamplifier.

There are two basic galvanic measurement techniques for E-field measurements in air. High impedance potential gradiometers require special attention to leakage currents and extremely high input impedances. Only recently have mass produced commercially available free space electric potential sensors become available. By comparison, low impedance charge induction (D-Dot) sensors may be constructed from simple and inexpensive off-the-shelf components such as metal plates and operational amplifier integrated circuits.

The low cost and simplicity makes D-Dot sensors attractive, but they have limitations and applications regarding both high sensitivity at low frequencies and small size because their sensitivity is proportional to both the rate of change of the ambient field and the electrode area used to collect the charge. Field mills have employed mechanical chopping of the E-field, typically at tens of hertz, and this modulation permits the ambient DC E-field to be sensed using an induction probe. However, the added size, weight, power, cost, and complexity of bulky drive motors, spinning shafts, and electromagnetic interference shielding of noisy drive components makes these field mills unappealing for small mobile applications or sensor arrays.

MEMS-technology offers the promise of low-cost production due to wafer-level processing. One problem with the previously known traditional MEMS E-field sensors lies in the unwanted interference signals generated by the high voltage electrostatic drive electronics. Thermal drives have been used, but these devices suffer from high power consumption.

A still further disadvantage of the previously known D-Dot sensors is that the output signal from the sensors often includes a high proportion of common mode signal. Thus, it is necessary to account for the common mode signals in order to obtain an accurate measurement of the magnitude of the E-field.

SUMMARY OF THE PRESENT INVENTION

The present invention provides an electric field sensor that overcomes all of the above-mentioned disadvantages of the previously known devices. In one embodiment, the electric field sensor of the present invention includes a substrate, made of any suitable material such as a silicon based material, which supports a sensor electrode constructed of an electrically conductive material. One or more pillars protrude outwardly from the sensor electrode, for instance, in a spaced-apart manner. The pillar(s) are constructed of electrically conductive material and can be formed as one piece with the sensor electrode.

A screen electrode overlies the sensor electrode. The screen electrode includes one or more openings so as to register with the one or more pillars, i.e., so that each pillar can extend through an associated opening on the screen electrode as the position of the screen electrode varies relative to the sensor electrode. The screen electrode is also constructed of an electrically conductive material.

At least one, and preferably several spaced piezoelectric actuators are connected between the substrate and the screen electrode. These piezoelectric actuators are powered or actuated by a voltage signal, such as a periodic voltage signal, so that the piezoelectric actuators modulate and displace the screen electrode toward and away from the sensor electrode at a frequency of the voltage signal. Consequently, as the piezoelectric actuators modulate the position of the screen electrode, the screen electrode moves from an upper position, in which the pillars are positioned beneath the screen electrode, and a lower position in which the pillars extend through the openings in the screen electrode. The use of piezoelectric actuators permits operation at low voltages, making this device easier to integrate with other low-power sensor circuitry. Moreover, the drive fields are contained in the piezoelectric material, so the drive fields are much lower than with conventional (electrostatic comb drive) techniques. And the piezoelectric actuators require very low power to drive as compared to thermal technique.

A circuit is electrically connected to both the screen electrode, which is electrically grounded, and the sensor electrode is configured to detect a voltage, a current output, or both, from the sensor electrode. In some embodiments, the circuit includes an operational amplifier having one input electrically connected to the screen electrode, its second input electrically connected to the sensor electrode, and a resistor electrically connected between the sensor electrode and an output from the operational amplifier so that the voltage output from the operational amplifier varies directly proportionally with the current from the sensor electrode.

A source of the electric signal modulates the position of the screen electrode relative to the sensor electrode preferably at a resonant frequency. Thus, when the electric field sensor of the present invention is positioned within an electric field, the current output from the sensor electrode would be lowest when the screen electrode is most spaced from the sensor electrode and effectively screening the sensor electrode from the electric field. Conversely, the current output from the sensor electrode will be maximum when the screen electrode is modulated to its closest position to the sensor electrode. When this occurs, the electric field acts directly on the pillars extending through the screen electrode thus inducing a current in the screen electrode which increases proportionally to the magnitude of the electric field. Consequently, the voltage output from the operational amplifier in the output circuit is proportional to the strength of the electric field.

At certain frequencies, the screen enters a mode of differential resonance. When this occurs, one area of the screen electrode moves in a direction toward the sensor electrode while a second area of the screen electrode moves away from the sensor electrode, and vice versa. Consequently, by splitting the sensor electrode into two separate sensor subelectrodes with one subelectrode aligned with the first screen electrode area and the second subelectrode aligned with the second screen electrode area, the differential outputs from the two subsensors are essentially doubled from that of a single electrode. Furthermore, by providing an output circuit for each sensor subelectrode, and combining those outputs together, the combined output of the electric field sensor effectively eliminates common mode signals.

In another embodiment of the invention, the sensor electrode includes a base having one or more fingers extending outwardly from one side of the base and across the top of the substrate, for instance, in a spaced apart and parallel manner. Similarly, the screen electrode also includes a base having one or more fingers which generally overlie the substrate and are registered, i.e., interdigitally positioned with respect to one or more fingers on the sensor electrode. A piezoelectric actuator is then coupled to at least the screen electrode, and preferably a second piezoelectric actuator coupled to the sensor electrode so that, when excited by an electric voltage signal, each piezoelectric actuator tilts its associated electrode relative to the base. When these two piezoelectric actuators are excited by a periodic voltage signal the sensor electrode and screen electrode pivot in opposite pivotal directions in synchronism with each other.

Thus, when the screen electrode is pivoted above the sensor electrode, the screen electrode effectively screens the sensor electrode from the electric field thus minimizing the signal output from the sensor electrode. Conversely, when the sensor electrode fingers are positioned above the screen electrode fingers, the current output from the sensor electrode is maximized. The screen electrode and sensor electrode are electrically connected to the output circuit in the previously described fashion.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 4 is a side view illustrating the electric field sensor of the present invention in a differential resonance mode;

FIG. 5 is a view similar to FIG. 1, but illustrating a second embodiment of the invention;

FIG. 6 is a side view of the second embodiment of the present invention with the screen electrode tilted above the sensor electrode; and FIG. 7 is a view similar to FIG. 6, but illustrating the sensor electrode tilted above the screen electrode.

DETAILED DESCRIPTION OF PREFERRED EMBODIMENTS OF THE PRESENT INVENTION

Figure 1:
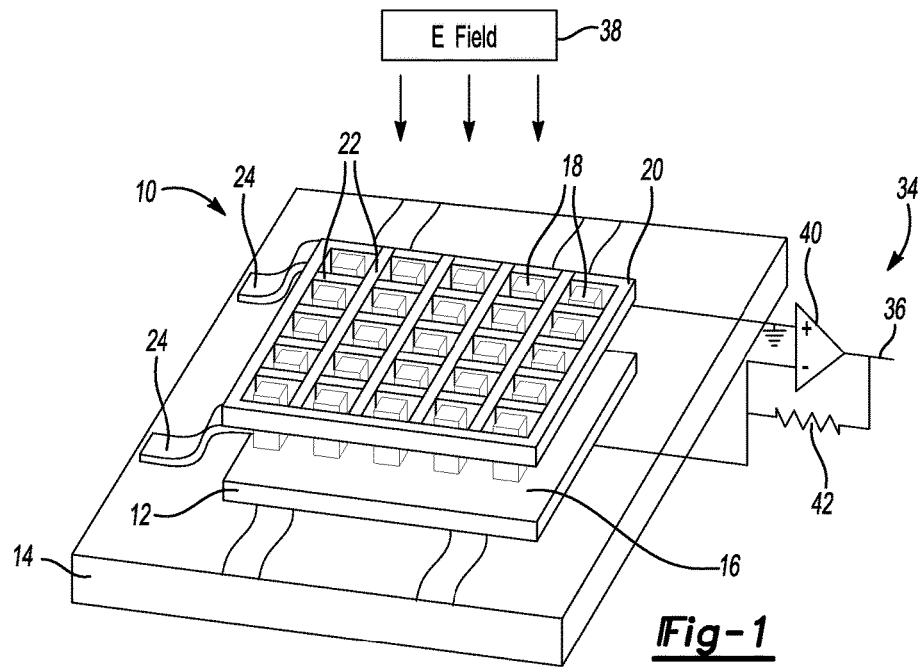
FIG. 1 is an elevational view illustrating a first embodiment of an electric field sensor according to the present invention.
Figure 2:
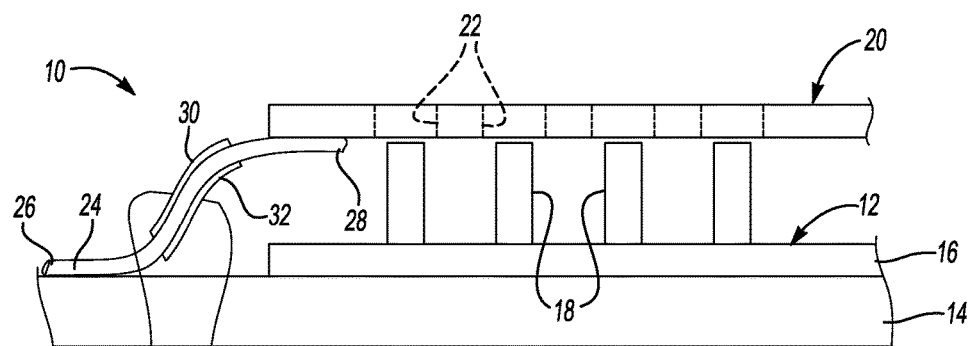
FIG. 2 is a side view of the electric field sensor of the present invention and illustrating the screen electrode in a position spaced from the sensor electrode.
Figure 3:
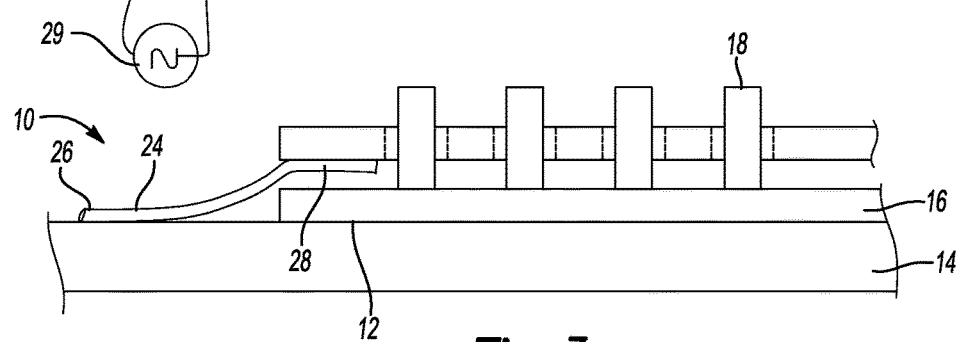
FIG. 3 is a view similar to FIG. 2, but illustrating the screen electrode in a close position relative to the screen electrode.

With reference first to FIGS. 1-3, a first embodiment of the electric field sensor 10 according to the present invention is shown. The electric field sensor 10 includes a sensor electrode 12 constructed of an electrically conductive material and supported on a substrate 14. The substrate 14 may be constructed of any conventional material, such as a silicon-based material.

The sensor electrode 12 includes a planar base 16 overlying and supported by the substrate 14. A plurality of spaced apart pillars 18 protrude outwardly from the base 16 so that the pillars 18 are spaced apart to each other, such as in a parallel or an orthogonal arrangement. The pillars 18 and sensor base 16 may be all of a one piece construction and may be formed, for instance, as a part of a Micro-Electro-Mechanical System (MEMS) processing step. While a plurality of pillars 18 is illustrated here, it will be appreciated that, in other embodiments, the electric field sensor 10 may include only a single pillar 18.

A screen electrode 20, also constructed of an electrically conductive material, overlies the sensor electrode 12. The screen electrode 20 also includes a plurality of openings 22 so that one opening 22 is aligned with each pillar 18 on the sensor electrode 12. Furthermore, the openings 22 in the screen electrode 20 are preferably complementary in shape, but slightly larger in size than, the cross-sectional size of the pillars 18. Consequently, each pillar 18 is able to pass, unobstructed, through its associated opening 22 in the screen electrode 20 as the screen electrode 20 moves from an upper position, illustrated in FIG. 2, and to a lower position, illustrated in FIG. 3. In its lower position, the pillars 18 protrude above the screen electrode 20. Of course, if the sensor 10 includes only one pillar 18, then only a single opening 22 will be needed.

In order to support the screen electrode 20 above the sensor electrode 12, at least one, and preferably several piezoelectric actuators 24 are provided. Each piezoelectric actuator 24 may be in the form of an elongated flat strip having one end 26 attached to the substrate 14 and its other end 28 attached to the screen electrode 20. The piezoelectric actuators 24 generally permit the screen electrode 20 to move relative to the sensor electrode 12 in an up and down manner. Although the number of piezoelectric actuators 24 may vary, as shown, the electric field sensor 10 is generally rectangular in shape with one piezoelectric actuator 24 attached adjacent each corner of the screen electrode 20.

In order to modulate the screen electrode 20 relative to the sensor electrode 12, i.e. to move the screen electrode 20 periodically between the position shown in FIGS. 2 and 3, a periodic voltage source 29 (FIG. 2) is electrically connected to piezoelectric electrodes 30 and 32 on opposed surfaces of the piezoelectric actuator 24 such as a sine wave, saw tooth wave, triangular wave, etc. Consequently, with the periodic voltage source 29 electrically connected to each of the piezoelectric electrodes 30 and 32 for each piezoelectric actuator 24, the position of the screen 20 will modulate in synchronism with the frequency, i.e. −10 kHz or 20 kHz, of the voltage source 29 between the upper and lower positions illustrated in FIG. 2 and FIG. 3.

With reference now to FIG. 1, an output circuit 34 is electrically connected to the sensor electrode 12 and screen electrode 20 which provides an output which varies in proportion with the strength of an electric field 38 (illustrated diagrammatically) acting on the electric field sensor 10.

In some embodiments of the invention, the output circuit 34 may include an operational amplifier 40 having its grounded input electrically connected to the screen electrode 20 and its other input electrically connected to the sensor electrode 12. A resistor 42 is electrically connected between the operational amplifier output 36 and the sensor electrode 12 so that the magnitude of the output voltage from the operational amplifier 40 is proportional to the current produced from the sensor electrode 12.

In operation, the modulation of the screen electrode 20 relative to the sensor electrode 12 causes the screen electrode to periodically block the electric field 38 from the sensor electrode 12 when the screen electrode 20 is in its upper position (FIG. 2), and expose the pillars 20 of the first electrode 12 to the electric field 38 when the screen electrode 20 is in its lower position (FIG. 3). When the screen electrode 20 blocks the electric field 38 from the sensor electrode 12, the current output from the sensor electrode 12 is minimized. Conversely, when the sensor electrode pillars 18 are exposed to the electric field when the screen electrode 20 is in its lower position (FIG. 3), the sensor electrode 12 will produce its maximum current output. By making many holes and pillars, the sensor area can be made larger (more sensitive), without increasing the distance that the screen travels to effectively modulate the field seen by the pillars. The magnitude of the current output from the sensor electrode 12 varies proportionally with the strength of the electric field 38. This variable current signal, furthermore, results in a varying voltage signal from the operational amplifier 40.

In order to determine the amount of current from the first sensor 12, an electric charge induction probe (or "D-Dot" sensor) senses an induced current i generated by a moving source charge (or more generally, by any time-varying E-field). The surface charge density $\rho_S$ induced on a conducting electrode at a free space interface due to exposure to an ambient E-field $E_n$ is $$\rho_S = D_n = \epsilon_0 E_n \quad (1)$$

$D_n$ and $E_n$ are the normal components of the electric flux and E-field vectors just outside the surface and $\epsilon_0$ is the permittivity of free space. The total charge Q on the conductor is obtained by integrating the induced $\rho_S$ over the electrode area A:

$$Q = \int \rho_S dA = \epsilon_0 E_n A_{eff} \quad (2)$$

where $A_{eff}$ is the effective area taking into account flux-concentration and modulation fraction effects. Equation (2) assumes 100% modulation of the measured field. If the screen is made to travel far enough to effectively shield and expose the pillars to the ambient field (near 100% modulation), then $A_{eff}$ can be slightly larger than the actual area A of the electrode. In any event, $A_{eff}$ varies with the distance from the nearest ground electrode. This charge induction effect may be measured as a current i:

$$i = \frac{dQ}{dt} = \frac{d(\epsilon_0 E_n A_{eff})}{dt} = \epsilon_0 A_{eff} \frac{dE_n}{dt}. \quad (3)$$

Assuming the sensed field $E_n$ is sinusoidal at a frequency f $$i = 2\pi f \epsilon_0 A_{eff} |E_n|. \quad (4)$$

Equations (3) and (4) show how the measured current of the D-Dot sensor depends strongly on the area of the electrode $A_{eff}$ and the rate of change of $E_n$ (and hence, the frequency f of $E_n$). Therefore, additional sensitivity can be obtained by modulating and measuring an E-field at a higher frequency. The practical upper limit of the modulating frequency is limited by the size of the sensor, the stiffness of the materials, and the degree of vacuum packaging.

With reference now to FIG. 4, at certain frequencies, which may be determined mathematically or empirically, of the periodic voltage source 28, the screen electrode 20 resonates in differential mode in which a first area 46 of the screen electrode 20 moves in a first direction, i.e. away from the sensor electrode 12, while a second area 48 of the screen electrode 20 moves in the opposite direction, i.e. toward the sensor electrode 12. In this event, the sensor electrode 12 may be divided into two subelectrodes 50 and 52 with the first area 46 of the screen electrode overlying the first subelectrode 50 while the second area 48 of the screen electrode 20 overlies the second electrode 52. One output circuit 34 is then electrically connected between the screen electrode 20 and the sensor subelectrode 52 while a second output circuit 34 is electrically connected between the screen electrode 20 and the second sensor subelectrode 50. The outputs from both output circuits 34 are then combined by a combiner circuit 54 to provide a combined signal on its output 56.

The differential mode operation depicted in FIG. 4 achieves two significant advantages over nondifferential resonance sensors. First, since the output current from the two sensor subelectrodes 50 and 52 is either increasing or decreasing in opposite directions when the electric field sensor is subjected to an electric field, the effective signal output from the combined sensor subelectrodes 50 and 52 essentially double the overall output from the individual sub-electrodes. In addition, however, since the areas 46 and 48 move in opposite directions, the coupling between the screen sensor areas 46 and 48 and the sensor subelectrodes 50 and 52 with their pillars 18 effectively cancel each other thus eliminating common mode noise from the output of the sensor. Although the combined effective area of the subelectrodes is reduced somewhat (relative to an equivalently-sized single electrode), the overall signal-to-noise ratio is expected to increase using this operational mode.

With reference now to FIGS. 5-7, a second embodiment of an electric field sensor 60 of the present invention is shown. The electric field sensor 60 includes a sensor electrode 62 having a base 64 and at least one, and preferably, a plurality of elongated spaced apart and parallel fingers 66 which extend outwardly from the base 64. The fingers 66 may integrally formed as a one piece construction with the base 64 in some embodiments.

Similarly, a screen electrode 68 also includes a base 70 and at least one, and preferably, a plurality of elongated spaced apart and parallel fingers 72 which extend outwardly from the base 70 and are of a one piece construction with the base 70. As best shown in FIG. 5, the fingers 66 and 72 of the sensor electrode 62 and screen electrode 68 are registered, i.e., interdigitally positioned with one screen electrode finger 72 positioned between each adjacent pair of sensor electrode fingers 66. With reference now particularly to FIGS. 6 and 7, a first piezoelectric actuator 74 supports the base 64 of the sensor electrode 62 to a substrate 76. Similarly, a second piezoelectric actuator 78 connects the base 70 of the screen electrode 68 to the substrate 76.

The piezoelectric actuators 74 and 78 operate in the same fashion as the piezoelectric actuator 24 (FIG. 1) in which the piezoelectric actuators 74 and 78 move their associated electrodes 62 and 68 periodically with a periodic voltage source, such as the voltage source 28 shown in FIG. 2. However, unlike the piezoelectric actuator 24, the piezoelectric actuators 74 and 78 cause the sensor electrode 62 and screen electrode 68 to tilt in opposite directions relative to each other.

For example, as shown in FIG. 6, when a voltage signal of one polarity is applied to the piezoelectric actuators 74 and 78, the piezoelectric actuator 74 tilts the sensor electrode 62 upwardly while, simultaneously, an opposite voltage applied to the piezoelectric actuator 78 tilts the screen electrode 68 downwardly. In doing so, the sensor electrode 62 is exposed to the maximum electric field 38 thus producing maximum current from the sensor electrode 62. This current is then received by the output circuit 34 (see FIG. 2) to generate an output signal representative of the strength of the electric field 38.

Conversely, when an opposite polarity signal is applied to the piezoelectric actuators 74 and 78, the piezoelectric actuators 74 and 78 tilt their respective sensor electrode 62 and screen electrode 68 in the opposite direction. In doing so, the screen electrode 68 is positioned above the sensor electrode 62 thus screening the sensor electrode 62 from the electric field 38 and minimizing the current output from the sensor electrode 62. This is shown in FIG. 7.

Still other configurations other than the sensor electrode and screen electrode configuration shown in FIGS. 1 and 5 are, of course, possible such as side to side or multimode. Furthermore, it will be understood that the entire sensor 60 can be manufactured as a MEMS structure so that the components of the sensors are on a microscopic level, e.g., on the order of about $10^{-6}$ meters. Furthermore, in order to provide a meaningful signal from the sensor, multiple sensors, either the electric field sensor 60 or the electric field sensor 10, can be synchronized in frequency and phase, and ganged together to provide a larger aggregate output signal. It is preferable to synchronize several smaller structures at a higher operating frequency, instead of operating one larger structure at a lower frequency, because the overall sensitivity can be made higher.

From the foregoing, it can be seen that the present invention provides a simple, yet effective, electric field sensor. Having described our invention, however, many modifications thereto will become apparent to those skilled in the art to which it pertains without deviation from the spirit of the invention as defined by the scope of the appended claims.

We claim:

1. An electric field sensor comprising:
a sensor electrode constructed of an electrically conductive material, said sensor electrode having one or more outwardly protruding pillars extending perpendicularly upwardly from a horizontal base surface,
a screen electrode overlying said sensor electrode, said screen electrode having one or more openings, said one or more openings configured to register with said one or more pillars,
at least one piezoelectric actuator connected to said screen electrode so that, when excited by a voltage signal, said at least one piezoelectric actuator is configured to move said screen electrode relative to said sensor electrode, and
an output circuit configured to detect a voltage, a current output, or both, between said sensor electrode and said screen electrode,
wherein a height of the one or more pillars from the base surface is greater than a thickness of the screen electrode,
wherein there are a plurality of pillars and a plurality of openings, and
wherein the one or more openings in the screen electrode are holes which each fully surround a corresponding pillar of the sensor electrode which it registers with.

2. The electric field sensor as defined in claim 1 wherein said sensor electrode is supported on a substrate.

3. The electric field sensor as defined in claim 2 wherein said at least one actuator has one portion attached to said substrate and a second portion attached to said screen electrode.

4. The electric field sensor as defined in claim 3 wherein said at least one actuator comprises a plurality of piezoelectric strips, each strip being attached to different areas of said screen electrode.

5. The electric field sensor as defined in claim 4 wherein each piezoelectric strip is flat and elongated, one end of each said strip being attached to said substrate and the other end of each said strip being attached to said screen electrode.

6. The electric field sensor as defined in claim 5 and comprising a first actuating electrode attached to a top of each piezoelectric strip and a second actuating electrode attached to a bottom of each piezoelectric strip, said periodic voltage signal being electrically connected to said actuating electrodes.

7. The electric field sensor as defined in claim 1 wherein said screen electrode is electrically grounded and wherein said output circuit comprises an operational amplifier having two inputs, one of said inputs being electrically connected to said screen electrode and the other of said inputs being electrically connected to said sensor electrode so that the magnitude of a voltage output of said operational amplifier is proportional to current produced by said screen electrode.

8. The electric field sensor as defined in claim 1 wherein said screen electrode is electrically grounded and wherein said output circuit comprises a differential amplifier having two inputs, one of said inputs being electrically connected to said screen electrode and the other of said inputs being electrically connected to said sensor electrode so that the magnitude of a voltage output of said amplifier is proportional to charge difference between said screen electrode and said sensor electrode.

9. The electric field sensor as defined in claim 1 wherein said sensor is a MEMS device on the order of about $10^{-6}$ meter.

10. The electric field sensor as defined in claim 1 wherein each of said pillars is complementary but smaller in size than its associated opening in said screen electrode.

11. The electric field sensor as defined in claim 10 wherein each pillar is rectangular in shape in cross section.

12. The electric field sensor as defined in claim 10 wherein each pillar is square in shape in cross section.

13. The electric field sensor as defined in claim 1 wherein a frequency of said voltage signal is selected to produce differential movement in two areas of said screen electrode and wherein said sensor electrode is divided into two sensor subelectrodes, a first of said two areas of said screen sensor overlying one subelectrode and a second of said two areas of said screen sensor overlying the other subelectrode.

14. The electric field sensor as defined in claim 13 comprising an output circuit associated with each sensor subelectrodes, with an output signal from both output circuits being combined to form a differential output signal for the electric field sensor.

15. The electric field sensor as defined in claim 1 wherein said screen electrode moves between an upper position in which said screen electrode is positioned fully above said one or more pillars forming a gap therebetween such that the screen electrode effectively blocks the electric field from the pillars of the sensor electrode thereby minimizing the current output from the entire sensor electrode, and a lower position in which said one or more pillars extend above said screen electrode thereby maximizing the current output from the entire sensor electrode.

16. The electric field sensor as defined in claim 15, the screen electrode moves with translational motion only relative to the sensor electrode between the upper and lower positions.

17. The electric field sensor as defined in claim 1, wherein the one or more pillars and the base of the sensor electrode are a one piece construction.

18. The electric field sensor as defined in claim 1, wherein the voltage signal is configured to modulate motion of the screen electrode at a resonant frequency of the sensor.

19. An electric field sensor comprising:
- a sensor electrode constructed of an electrically conductive material, said sensor electrode having one or more outwardly protruding pillars extending perpendicularly upwardly from a horizontal base surface,
- a screen electrode overlying said sensor electrode, said screen electrode having one or more openings, said one or more openings configured to register with said one or more pillars,
- at least one piezoelectric actuator connected to said screen electrode so that, when excited by a voltage signal, said at least one piezoelectric actuator configured to move said screen electrode relative to said sensor electrode, and
- an output circuit configured to detect a voltage, a current output, or both, between said sensor electrode and said screen electrode,
- wherein a height of the one or more pillars from the base surface is greater than a thickness of the screen electrode,
- wherein said screen electrode moves between an upper position in which said screen electrode is positioned fully above said one or more pillars forming a gap therebetween such that the screen electrode effectively blocks the electric field from the pillars of the sensor electrode thereby minimizing the current output from the entire sensor electrode, and a lower position in which said one or more pillars extend above said screen electrode thereby maximizing the current output from the entire sensor electrode.

20. A method of operating the electric field sensor as defined in claim 1, the method comprising:
- applying a periodic voltage signal to the at least one actuator so that said at least one piezoelectric actuator modulates said screen electrode toward and away from said sensor electrode at the frequency of said periodic voltage signal.

* * * * *